US012756329B2

(12) United States Patent
Bierg et al.

(10) Patent No.: US 12,756,329 B2
(45) Date of Patent: Oct. 6, 2026

(54) IMPLANTABLE MEDICAL DEVICE COMPRISING A DC-DC CONVERTER

(71) Applicant: SORIN CRM SAS, Clamart (FR)

(72) Inventors: Jean-Claude Bierg, Coubron (FR); Marc Laflutte, Versailles (FR); Paul Giraud, Asnieres-sur-Seine (FR); Emmanuel Béguin, Montigny-le-Bretonneux (FR)

(73) Assignee: SORIN CRM SAS, Clamart (FR)

( * ) Notice: Subject to any disclaimer, the term of this patent is extended or adjusted under 35 U.S.C. 154(b) by 158 days.

(21) Appl. No.: 18/267,420

(22) PCT Filed: Dec. 13, 2021

(86) PCT No.: PCT/EP2021/085465
§ 371 (c)(1),
(2) Date: Jun. 14, 2023

(87) PCT Pub. No.: WO2022/128903
PCT Pub. Date: Jun. 23, 2022

(65) Prior Publication Data
US 2024/0100350 A1 Mar. 28, 2024

(30) Foreign Application Priority Data
Dec. 14, 2020 (FR) ....................................... 2013199

(51) Int. Cl.
*H02M 3/335* (2006.01)
*A61N 1/39* (2006.01)
*H02M 7/10* (2006.01)

(52) U.S. Cl.
CPC .......... *H02M 7/103* (2013.01); *A61N 1/3956* (2013.01); *H02M 3/33507* (2013.01)

(58) Field of Classification Search
CPC ............................................... H02M 3/335–42
See application file for complete search history.

(56) References Cited

U.S. PATENT DOCUMENTS 3,243,683 A * 3/1966 Ackley ................. H02M 7/103 363/60
3,928,793 A * 12/1975 Waltz .................. H02M 3/3381 363/19

(Continued)

FOREIGN PATENT DOCUMENTS

JP S63234871 A 9/1988
JP 2017017845 A 1/2017
WO 2010144528 A2 12/2010

OTHER PUBLICATIONS

Antonini et al., "A Modular Optically Powered Floating High Voltage Generator," Review of Scientific Instruments, vol. 84, 2013, 5 pages.

(Continued)

*Primary Examiner* — Peter M Novak

(57) ABSTRACT

The present invention relates to a step-up converter with a plurality of levels, in particular for use in an implantable medical device, comprising a transformer (11) comprising a single primary winding and a single secondary winding; a primary circuit (6) comprising the single primary winding; and a secondary circuit (7) comprising the single secondary winding and a plurality of step-up levels, each of the step-up levels comprising a first diode (4*a*, 4*b*, 4*c*, 4*d*, 4*e*, 4*f*) and a second diode (10*a*, 10*b*, 10*c*, 10*d*, 10*e*, 10*f*) and a first capacitor (9*a*, 9*b*, 9*c*, 9*d*, 9*e*, 9*f*) and a second capacitor (3*a*, 3*b*, 3*c*, 3*d*, 3*e*, 3*f*), wherein the first capacitors (9*a*, 9*b*, 9*c*, 9*d*, 9*e*, 9*f*) of the plurality of step-up levels are connected in series or in parallel with one another. The present invention also relates to an implantable medical device comprising the step-up converter with a plurality of levels mentioned above, and a method for using the step-up converter with a plurality of levels or the implantable device mentioned above.

14 Claims, 9 Drawing Sheets

(56) References Cited

U.S. PATENT DOCUMENTS

| | | | | |
|---|---|---|---|---|
| 5,521,807 | A * | 5/1996 | Chen | H02M 3/33538 363/21.04 |
| 8,971,058 | B2 * | 3/2015 | Pan | H02M 3/33569 363/21.04 |
| 2003/0048643 | A1 * | 3/2003 | Lin | H02M 1/36 363/21.06 |
| 2011/0103102 | A1 * | 5/2011 | Chiang | H02M 3/335 363/21.13 |
| 2018/0301998 | A1 | 10/2018 | Fogel | |
| 2021/0099092 | A1 * | 4/2021 | Basso | H02M 3/33523 |
| 2021/0315080 | A1 * | 10/2021 | Zhou | H02M 3/33507 |

OTHER PUBLICATIONS

Chung et al., "A CW CO2 Laser Using a High-Voltage DC-DC Converter with Resonant Inverter and Cockroft-Walton Multiplier," Optics and Laser Technology, Elsevier Science Publishers BV, Amsterdam, NL, vol. 38, No. 8, Nov. 1, 2006, pp. 577-584.

Hosain et al., "Radio Frequency Energy Harvesting From a Feeding Source in a Passive Deep Brain Stimulation Device for Murine Preclinical Research," Medical Engineering & Physics, vol. 37, No. 10, Oct. 2015, pp. 1020-1026.

International Search Report, PCT/EP2021/085465, Mar. 16, 2022, 7 pages.

Katzir et al., "A Split-Source Multisection High-Voltage Power Supply for X-Ray," IEEE Journal of Emerging and Selected Topics in Power Electronics, IEEE, Piscataway, NJ, USA, vol. 4, No. 2, Jun. 1, 2016, pp. 373-381.

Raymond et al., "27.12 MHz Isolated High Voltage Gain Multi-Level Resonant DC-DC Converter," 2015 IEEE Energy Conversion Congress and Exposition (ECCE), IEEE, Sep. 20, 2015, pp. 5074-5080.

Tang et al. "A Fully Implantable Wireless Neural Interface for Simultaneous Recording from Multiple Sites of Peripheral Nerves in Free Moving Animal," 2017 IEEE International Conference on Cyborg and Bionic Systems (CBS), IEEE, Oct. 17, 201, pp. 160-164.

Zhiguo et al., "Analysis and Design of Isolated Flyback Voltage-MultiplierConverter for Low-Voltage Input and High-Voltage Output Applications," IET Power Electronics, The Institution of Engineering and Technology, vol. 6, No. 6, 2013, pp. 1100-1110.

* cited by examiner

IMPLANTABLE MEDICAL DEVICE COMPRISING A DC-DC CONVERTER

The present invention relates to an implantable medical device, in particular, an implantable defibrillator, which comprises a DC-DC converter used to charge surge capacitors.

Medical devices, for example, cardioverters and defibrillators, are used to provide electrical pulses to perform therapy to the heart of a patient in the form of pacing and/or defibrillation shocks. Defibrillation shocks may be administered to treat tachycardia or ventricular/atrial fibrillation. The implantable medical device may comprise certain circuitry that is configured to sense medical conditions, such as fibrillation events, that require pacing and/or a therapeutic electric shock. The electrodes implanted in the body of the patient provide the electrical stimuli in a programmable manner.

Generally, a DC-DC (DC meaning direct current) converter is required to convert the electrical energy supplied by a low voltage DC power source to a high voltage energy level stored in one or more high energy storage capacitors.

A typical form of DC-DC converter is commonly referred to as a "flyback" converter as shown in FIG. 1*a*. The flyback converter comprises a primary circuit 6 that is supplied by a primary supply 1, such as a battery, and uses a transformer 5 having a primary winding or coil in series with the primary supply 1. The primary circuit 6 further comprises a switching device, for example, a transistor device, or an interrupt circuit 2 in series with the primary coil and the battery 1. The flyback converter further comprises secondary circuits 7*a*, 7*b* comprising a plurality of secondary windings and diodes 4*a*, 4*b* in series with high energy capacitors 3*a*, 3*b*.

The charging of a high energy capacitor is achieved by inducing a voltage in the primary winding of the transformer creating a magnetic field in the secondary windings. When the current in the primary winding is interrupted, whereas the magnetic flux in the transformer cannot have any discontinuities, a current is created in the secondary windings of the transformer 5, which current is applied to the high-energy capacitors 3*a*, 3*b* to charge them. The repeated interruption of the supply current gradually charges the high-energy capacitors 3*a*, 3*b*.

Flyback converters comprising more than two secondary windings in order to achieve a sufficiently high output voltage depending on the voltage withstand of the surge capacitors as shown, for example, in FIG. 1*b* with three secondary windings, do however suffer from an architecture that is difficult to bring to industrial scale due to the number of windings on the transformer. As a consequence, there is a need for a DC-DC converter for an implantable medical device that allows for the voltage of an implemented primary power source to be increased in an architecture that can more readily be brought to industrial scale.

The present invention addresses the above need by providing a step-up converter with a plurality of levels, or a so-called multilevel flyback converter for use in an implantable medical device, for example, an implantable defibrillator. The step-up converter with a plurality of levels comprises a transformer comprising a single primary winding and a single secondary winding. The step-up converter with a plurality of levels further comprises a primary circuit comprising the single primary winding and a secondary circuit comprising the single secondary winding and a plurality of step-up levels. Each of the step-up levels comprises a first diode and a second diode and a first capacitor or coupling capacitor and a second capacitor or surge capacitor.

The configuration that is thus provided combines the transformer approach of a flyback converter architecture with an architecture with a plurality of step-up levels. Inasmuch as only one secondary winding is required, the resulting architecture is advantageous when compared to conventional flyback converters.

The primary circuit may comprise a primary power source connected in series with the first winding of the transformer and a switching device connected in series with the first winding. The primary power source may consist of or comprise a battery supplying a DC voltage. The voltage of the battery may be, for example, in the range of a few Volts (V).

According to one embodiment, the primary circuit may additionally comprise an inductor. Said inductor is in series with the transformer and allows for a reduction in the occurrence of a current surge when the switching device is closed. By reducing this current surge, components such as the switching device and the transformer can be protected against degradation, which improves reliability.

A step-up level can only comprise one capacitor, with one terminal of the capacitor being directly connected to one terminal of the single secondary winding, and only one diode linking the other terminal of the capacitor to the other terminal of the single secondary winding. By eliminating one coupling capacitor and one diode compared to the other step-up levels, it becomes possible to reduce the number of components without observing a significant difference in the functionality of the device. The device can thus be realized with a smaller footprint, which is an advantage when used in a medical device.

In at least one step-up level, in particular in each of the step-up levels of the secondary circuit, the anode of the first diode may be connected to one of the terminals of the first capacitor and to the cathode of the second diode, one of the terminals of the second capacitor may be connected to the cathode of the first diode, and the other terminal of the second capacitor may be connected to the anode of the second diode between the first and second capacitor and in series with the first and second capacitor.

The second capacitors of each of the plurality of step-up levels may be connected in series with one another to provide relatively high voltage outputs, for example, for defibrillation shocks.

In principle, the step-up converter with a plurality of levels may be configured to step up a voltage of the primary power source from a primary voltage in the range of 1 V to 9 V to an output voltage provided by the secondary capacitors of the step-up levels in the range of 10 V to 100 V or in the range of 100 V to 2000 V. The ratio of primary winding turns to single secondary winding turns must be appropriately selected.

In one embodiment, the turn ratio of the first winding np to the single secondary winding ns may be $ns/np \geq 2$. This allows for the use of a low voltage switching device. This allows for the reduction of the size of the component and thus the volume of the implantable medical device. Moreover, lower switching losses are observed when compared to switching devices that maintain higher voltages, which improves the efficiency of the converter.

Due to the configuration comprising the first circuit comprising the first transformer winding and the second circuit comprising the second transformer winding, a galvanic isolation of the primary circuit from the secondary circuit is achieved.

The switching device may comprise a transistor device. For example, a MOSFET device. A relatively low channel resistance of the MOSFET device is more easily achieved since the switching device does not need to withstand a high voltage but rather a voltage much lower than the output voltage. Thus, the turn ratio allows for a relaxation of the voltage withstand constraint of the switching device and reduces the switching losses for a given channel resistance.

In addition, in all of the embodiments described above, the primary circuit may comprise a capacitor connected in parallel to a primary power source, such as a battery.

In all the embodiments described hereinabove, the primary circuit may comprise a first sensing means to sense a current that flows in the first winding and a second sensing means to sense oscillations at the terminals of the switching device.

Moreover, it should be noted that, in principle, more than one transformer may be comprised in the step-up converter with a plurality of levels of the embodiments described hereinabove. The step-up converter with a plurality of levels may thus comprise another transformer comprising another primary winding, in particular, another single primary winding, and another secondary winding, in particular, a single secondary winding.

In one embodiment, the first capacitors of the step-up levels of the secondary circuit may be connected in parallel or in series with each other. A parallel connection of the capacitors may allow for the achievement of voltages provided by the capacitors that are better balanced compared to a series connection of the capacitors.

The present invention also addresses the above need by providing a step-up converter with a plurality of levels for use in an implantable medical device, for example, an implantable defibrillator, in particular, a subcutaneous implantable defibrillator, the step-up converter with a plurality of levels comprising a transformer comprising at least two secondary windings, in particular, two secondary windings, and a plurality of step-up levels.

The invention thus also relates to a step-up converter with a plurality of levels, for use in an implantable medical device, comprising a transformer comprising a single primary winding and at least two secondary windings; a primary circuit comprising the single primary winding and a secondary circuit, preferably galvanically isolated from the first circuit, comprising the secondary windings and a plurality of step-up levels each being associated with one of the secondary windings, a step-up level, in particular each step-up level, comprising a first diode and a second diode and a first capacitor and a second capacitor. Each of the plurality of step-up levels can be associated with its secondary winding only in a bijective relationship.

In the configuration of the two parallel secondary windings, the maximum charge of the first capacitors charged at the highest level can be reduced compared to the embodiments described hereinabove. The primary circuit and individual step-up levels may be configured in the same manner as in the embodiments described hereinabove.

For example, in at least one step-up level, in particular in each step-up level, the anode of the first diode may be connected to one of the terminals of the first capacitor and to the cathode of the second diode, one of the terminals of the second capacitor may be connected to the cathode of the first diode, and the other terminal of the second capacitor may be connected to the anode of the second diode. The second capacitors of each of the plurality of step-up levels may be connected in series with each other and/or the first capacitors may be connected in series or in parallel with each other.

This alternative configuration comprising at least two secondary windings may also be configured to step up a voltage of the first power source from a primary voltage in a range of 1 V to 9 V to an output voltage provided by the second capacitors of the step-up levels in a range of 10 V to 100 V or a range of 100 V to 2000 V.

One of the first step-up levels may comprise only one capacitor, with one terminal of the capacitor directly coupled to one terminal of the secondary winding, and only one diode linking the other terminal of the capacitor to the other terminal of the same secondary winding. Due to the elimination of one coupling capacitor and one diode when compared to the other step-up levels, it becomes possible to reduce the number of components without observing a notable difference in the functionality of the device. The device can thus be realized with a smaller footprint which is an advantage when used in a medical device.

The invention moreover relates to an implantable medical device comprising the step-up converter with a plurality of levels according to one of the embodiments described hereinabove. The implantable medical device may consist of or comprise an implantable defibrillator that is configured to provide electrical shocks and/or pacing by discharging the second capacitors of the step-up levels of the secondary circuit of the step-up converter with a plurality of levels. The implantable defibrillator may comprise defibrillation and sensing electrodes and a housing and a lead. The implantable defibrillator may be configured to generate an electric field at the location of the heart of a patient without the need to attach defibrillation electrodes to the heart chamber, which is to say, that the defibrillation electrodes may be located outside the heart chamber.

Moreover, the invention likewise relates to a method of operating of the embodiments described hereinabove of a step-up converter with a plurality of levels or the above-mentioned implantable device, wherein the method comprises the steps of:

a) closure of the switching device of the step-up converter with a plurality of levels for a first period of time such that the first winding stores energy according to a peak value of an electric current flowing in the primary circuit and such that the first capacitors are charged to the voltages of the second capacitors;

b) opening the switching device of the step-up converter with a plurality of levels during a second period of time, in particular, immediately after the first period of time, so that the energy is transferred to the second capacitors by means of the first capacitors; and repeating steps a) and b) above, which is to say closure of the switching device during the first period of time and opening it during the second period of time, until a predefined output voltage can be supplied by the second capacitors.

Moreover, the invention likewise relates to a method of operating of the embodiments described hereinabove of a step-up converter with a plurality of levels or the above-mentioned implantable This method allows for variations in current in the secondary winding to be divided by the turn ratio and the secondary times to be multiplied by this same turn ratio. The electromagnetic disturbances are thus greatly reduced compared to a conventional flyback converter.

The diodes described hereinabove are connected in such a way as to facilitate the execution of the steps of the method.

The method may moreover comprise discharging the second capacitors in order to generate an electrical pulse that can be delivered by means of electrodes. The energy stored in the second capacitors may thus be used to deliver a shock.

According to one embodiment, the duration of the first period increases, in particular in a progressive manner, over all or part of the iterations of steps a) and b). According to another embodiment, the maximum of the current Ip in the primary circuit may increase, in particular in a progressive manner, over all or part of the iterations of steps a) and b). This allows for a reduction in the occurrence of a current surge when the switching device is closed. By reducing this current surge, components such as the switching device and the transformer can be protected against degradation, which improves reliability.

Additional features and advantages of the present invention will be described with reference to the drawings. In the description, reference is made to the appended figures which are intended to illustrate preferred embodiments of the invention. It is understood that such embodiments do not represent the full scope of the invention.

FIG. 1*a* represents a first example of a flyback converter of an implantable medical device according to the state of the art.

FIG. 1*b* represents a second example of a flyback converter of an implantable medical device according to the state of the art.

FIG. 2*a* represents a step-up converter with a plurality of levels of an implantable medical device comprising a transformer and step-up levels according to a first embodiment of the present invention.

FIG. 2*b* shows a step-up converter with a plurality of levels of an implantable medical device comprising a transformer and step-up levels according to a variant of the first embodiment of the present invention.

FIG. 2*c* shows the signal at the gate of the MOSFET as a function of time.

FIG. 2*d* shows the current Ip in the first circuit 6 as a function of time.

The present invention relates to a step-up converter with a plurality of levels, or even a multilevel flyback converter for stepping up a DC voltage supplied by a primary power source of an implantable medical device. According to one embodiment, the step-up converter with a plurality of levels comprises a transformer comprising a single primary winding and a single secondary winding and a plurality of step-up levels.

According to another embodiment, the step-up converter with a plurality of levels comprises a transformer comprising one single primary winding and at least two secondary windings, in particular two secondary windings, and a plurality of step-up levels.

Figure 2A:
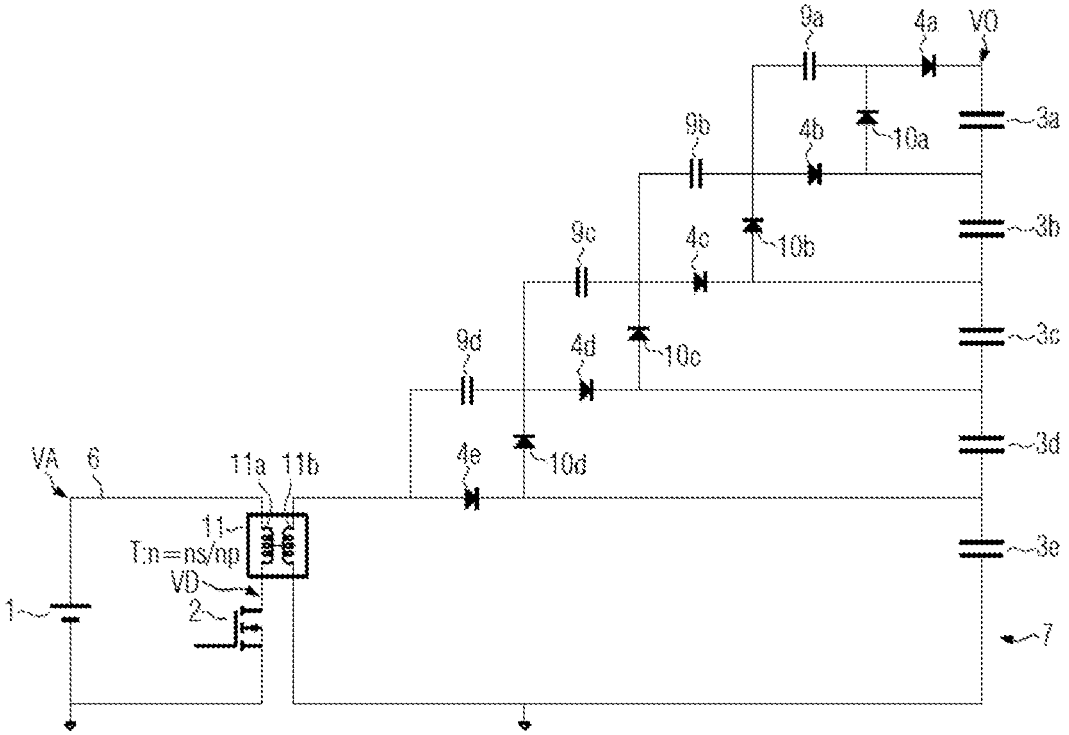

An example of one embodiment of a step-up converter with a plurality of levels is shown in FIG. 2*a*. The step-up converter with a plurality of levels comprises a primary circuit 6, at low voltage, and a secondary circuit 7, at high voltage, which are galvanically isolated from each other. The primary circuit 6 comprises a primary power source 1, in particular, a DC source, for example, a battery or a plurality of batteries in series. The battery may be, for example, a lithium-manganese dioxide battery or a lithium-carbon monofluoride battery or a lithium-silver vanadium oxide battery and may provide a battery voltage VA in the range of 3 V, 6 V or 9 V. Moreover, the primary circuit 6 comprises a switching device 2, for example, comprising a transistor device, in particular, a MOSFET transistor.

The step-up converter with a plurality of levels comprises a transformer 11. The transformer 11 comprises a single primary winding 11*a* with np turns or coil as part of the primary circuit 6 and a single secondary winding 11*b* with ns turns or coil as part of the secondary circuit 7. The ratio ns/np is preferably greater than or equal to 2. The secondary circuit 7 comprises several step-up levels, the number of which levels is not restricted. The step-up levels comprise a first plurality of capacitors 9*a*, 9*b*, 9*c*, 9*d*, also referred to as coupling capacitors, and a second plurality of capacitors 3*a*, 3*b*, 3*c*, 3*d*, also referred to as surge capacitors. Moreover, the step-up levels of the secondary circuit 7 comprise a first plurality of diodes 4*a*, 4*b*, 4*c*, 4*d* and a second plurality of diodes 10*a*, 10*b*, 10*c*, 10*d*. The diodes 10*a*, 10*b*, 10*c*, 10*d* allow for charging of the coupling capacitors whereas the diodes 4*a*, 4*b*, 4*c*, 4*d* charge the surge capacitors.

The secondary circuit 7 comprises an additional step-up level with a fifth capacitor 3*e* and a further diode 4*e* without coupling capacitor and without second diode. One terminal of the capacitor 3*e* is coupled directly to single secondary winding 11*b*, the other terminal of the capacitor 3*e* to the diode 4*e* which is configured to pass current from the single secondary winding 11*b* to the capacitor 3*e*. Due to the elimination of one coupling capacitor and one diode it becomes possible to reduce the number of components without observing a notable difference in the functionality of the device. The device can thus be realized with a smaller footprint which is an advantage when used in a medical device.

The second plurality of capacitors 3*a*, 3*b*, 3*c*, 3*d* and the fifth capacitor 3*e* are connected in series with each other and provide the high output voltage VO. The output voltage VO therefore depends on the number of step-up levels and the duty cycle of the charging process (see description below).

The individual connections of the various capacitors and diodes to each other are illustrated in more detail in the electrical circuit in FIG. 2*a*. By way of example, for the step-up level comprising elements 3*a*, 4*a*, 9*a* and 10*a*, the connections are as follows, including those with the neighboring step-up level. One terminal of the coupling capacitor 9*a* is connected to the cathode of the diode 10*a* and to the anode of the diode 4*a*. The cathode of the diode 4*a* is connected to the positive terminal of the capacitor 3*a*. The anode of the diode 10*a* and the cathode of the diode 4*b* of the adjacent step-up level are connected to the negative terminal of capacitor 3a. The other terminal of capacitor 9a is connected to the anode of the diode 4b, of one terminal of capacitor 9b, and the cathode of the diode 10b of the neighboring step-up level. The negative terminal of capacitor 3a is connected to the positive terminal of the neighboring capacitor 3b.

The diode 4a is thus configured to allow the current flow towards the surge capacitor 3a. The second diode 10a is configured to allow the current flow in the direction of the capacitor 9a.

An exemplary mode of operation of the step-up converter with a plurality of levels shown in FIG. 2a is as follows. During a first period of time, called primary phase, the switching device 2 is in the closed position. During the first period, the difference of the voltage VA supplied by the primary power source 1 and a voltage VD close to earth is applied to the first winding 11a of the transformer 11. The current rises to a maximum value Ipmax in the first circuit 6 and the first winding in the first period of time and, thus, the energy stored in the first winding reaches a value of approximately 0.5 $Ipmax^2$ Lp, where Lp denotes the inductance of the first winding 11a. During the first period of time, as regards the secondary circuit 7, the coupling capacitors 9a through 9d are charged to the voltages of the output capacitors 3b through 3e by means of the diodes 10a through 10d. As soon as the coupling capacitors 9a through 9d are fully charged, the current flowing in the single secondary winding of the transformer 11 is nil due to the presence of the diodes 4a through 4e.

In a second period of time immediately following the first period of time, the switching device 2 is in an open state. By switching the switching device 2 into the open state, the current flow in the first circuit 6 of the step-up converter with a plurality of levels is interrupted. As a consequence, a current is induced in the second winding 11b of the transformer 11 and the secondary circuit 7. Energy is therefore transferred to the output capacitors 3a through 3e by means of the coupling capacitors 9a through 9d and the diodes 4a through 4e.

After the output capacitors 3a through 3e have stored the electrical energy supplied by the coupling capacitors 9a through 9d and the second winding 11b, the cycle is repeated until a desired predefined output voltage VO can be supplied by the output capacitors 3a through 3e.

The control of the switching device 2 can be effected by a control unit and the switching of the switching device can be based on signals provided, for example, by an oscillator circuit.

Figure 2B:
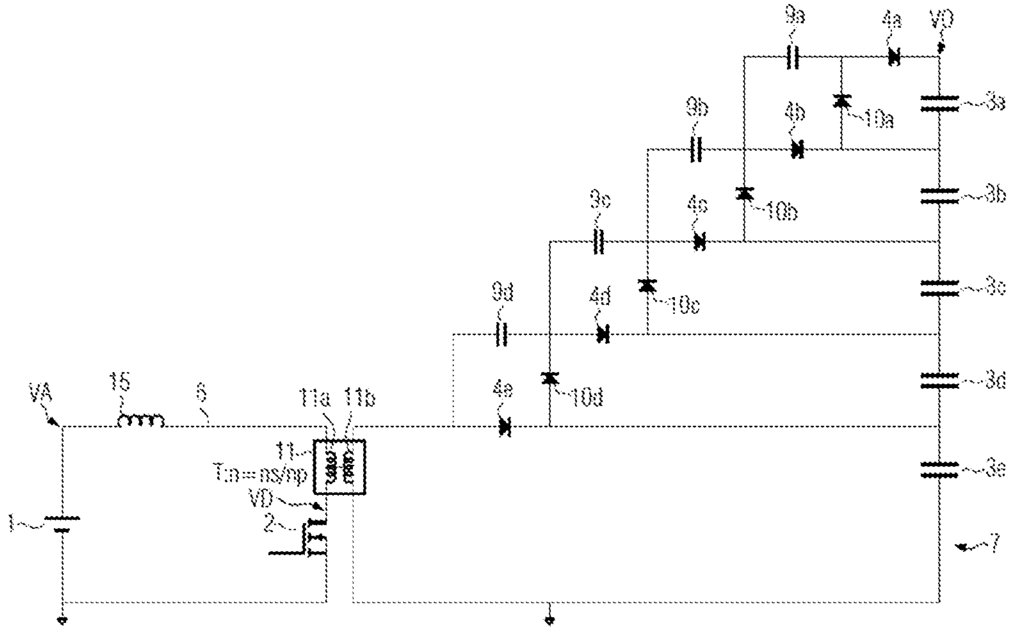

Another embodiment of a step-up converter with a plurality of levels similar to the one described hereinabove and similar in operation is shown in FIG. 2b. Similar elements are indicated by the same reference numbers.

When compared to the converter of FIG. 2a, the first circuit 6 additionally comprises an inductor 15 in series with the primary winding 11a and the switching device 2.

The presence of this inductance 15 allows for a reduction in the occurrence of a current surge when the switching device 2 is closed at the beginning of the first period described above. When the primary switch is closed in the first period, there is a voltage jump across the terminals of the single secondary winding 11b of the transformer 11, which causes a current surge in the recharge current Is of the coupling capacitors of the secondary circuit 7. This current surge is, moreover, multiplied by the turn ratio.

Figure 2C:
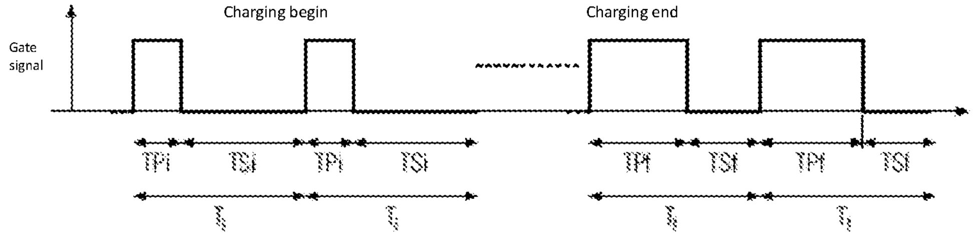
Figure 2D:
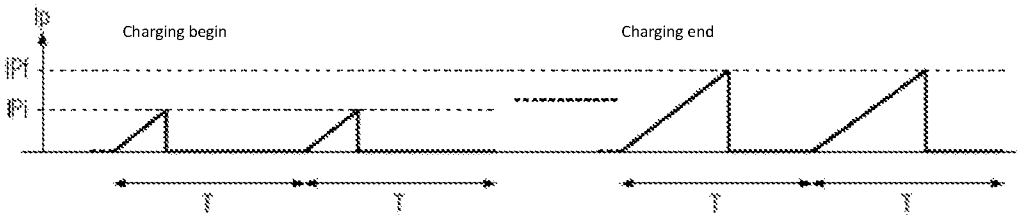

FIG. 2c and FIG. 2d illustrate two other methods for reducing the problem of the current surge in the primary period. Both methods may be realized by the converter according to FIG. 2a or according to FIG. 2b.

FIG. 2c shows the signal at the gate of the MOSFET as a function of the time at the beginning i and at the end f of a charging cycle of the surge capacitors 3a through 3e. FIG. 2c shows a charging principle with control of the duration of the first period Tp in relation to the duration of the second period Ts as a function of the time. The control of the duration of the primary period Tp during charging allows for the management of the current surge. We start with a first period Tpi that is low compared to the second period Tsi and we progressively increase its value over all or part of the charge. Towards the end of the charging of the surge capacitors, Tpf is greater than Tpi, while the second duration at the end Tsf is shorter than at the beginning Tsi. The duration of Ts can likewise evolve independently of Tp during the charging. As a consequence, T=Tp+Ts may likewise evolve during the charging of the capacitors, therefore Ti at the beginning of charging may be different from Tf at the end of charging.

FIG. 2d shows the current Ip in the first circuit 6 as a function of time. FIG. 2d therefore shows a charging principle with control of the primary current Ip. The control of the current Ip during charging likewise allows the management of the current surge. At the beginning of a charging cycle of the surge capacitors 3a through 3e, the maximum current Ipi in the primary circuit 6 is low and gradually increases its value over all or part of the charge until reaching a value 1pf>Ipi at the end of the cycle.

It is also conceivable to combine the approaches of FIG. 2c and FIG. 2d.

Figure 3:
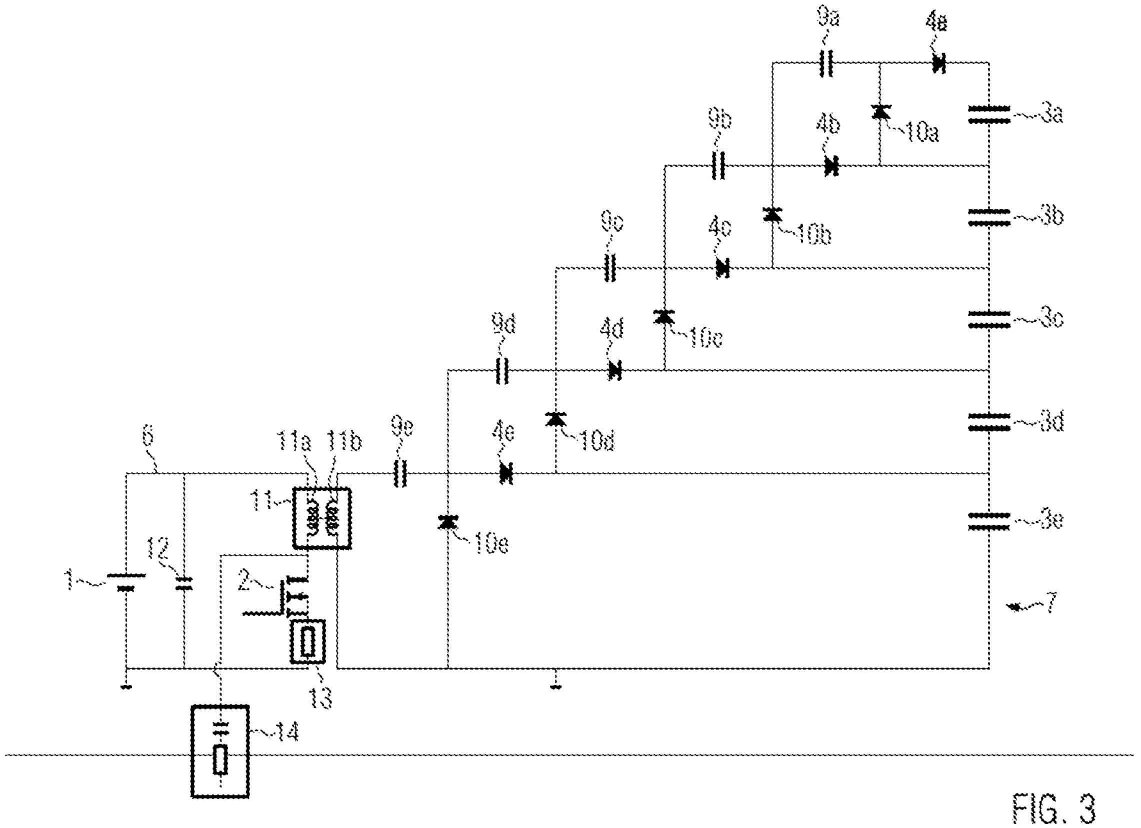
FIG. 3 shows a step-up converter with a plurality of levels of an implantable medical device comprising a transformer and step-up levels according to a second embodiment of the present invention.

Another embodiment of a step-up converter with a plurality of levels that is similar to the one described hereinabove and similar in operation is illustrated in FIG. 3. Similar elements are indicated by the same reference numbers.

The step-up converter with a plurality of levels shown in FIG. 3 comprises a primary circuit 6 and a secondary circuit 7 which are galvanically isolated from each other. The primary circuit 6 comprises a primary power source 1, in particular a DC source, for example a battery or a series of batteries and a switching device 2, for example a MOSFET. The primary circuit moreover comprises a capacitor 12 connected in parallel to the primary power source 1. The capacitor 12 has a function of filtering the current of the primary power source 1.

Moreover, the primary circuit 6 comprises a first sensing means 13 for sensing the current flowing in the first winding and a second sensing means 14 for sensing of secondary oscillations at the end of the second period, which oscillations are sensed at the terminals of the switching device. The charge cycles can be controlled based on the signals respectively provided by the devices 13 and 14 for primary and secondary sensing. The end of the first period will intervene when the current through device 13 has reached a predefined value. The end of the second period will intervene when device 14 has sensed the oscillations that appear on the drain of the MOSFET at the moment in which the energy stored in the transformer 11 has been completely drained towards the surge capacitors.

The secondary circuit 7 comprises a first plurality of coupling capacitors 9a, 9b, 9c, 9d, 9e and a second plurality of (surge) capacitors 3a, 3b, 3c, 3d, 3e. In addition, the secondary circuit 7 comprises a first plurality of diodes 4a, 4b, 4c, 4d, 4e and a second plurality of diodes 10a, 10b, 10c, 10d, 10e. The individual connections of the various diodes and capacitors to each other can be seen in detail from the circuit of FIG. 3 and correspond to those of FIG. 2*a*.

In this embodiment, all the step-up levels therefore comprise a coupling capacitor, a surge capacitor and two diodes.

According to a variant, an inductance can be introduced in the primary circuit 6 as in the variant shown in FIG. 2*b* to reduce the current surge at the beginning of the primary period.

Figure 4:
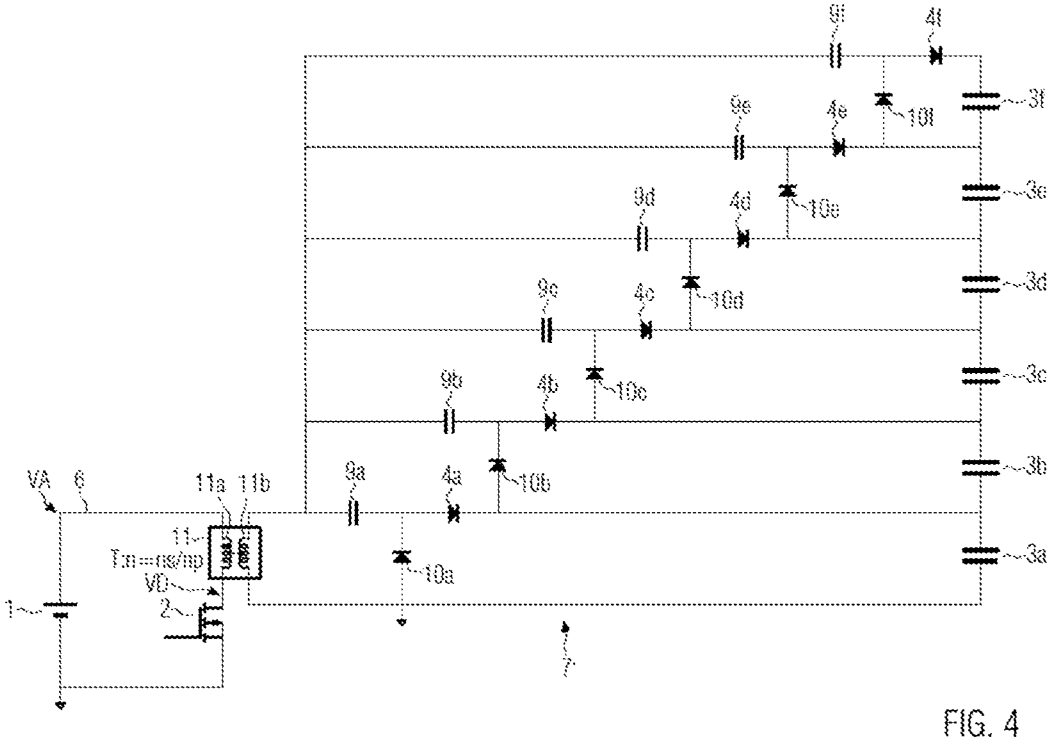
FIG. 4 represents a step-up converter with a plurality of levels of an implantable medical device comprising a transformer and step-up levels according to a third embodiment of the present invention.

Another embodiment example of a step-up converter with a plurality of levels is shown in FIG. 4. This embodiment is similar to the other embodiments shown in FIG. 2*b* and in FIG. 3. The primary circuit 6 of the embodiment of FIG. 4 is the same as the one of the embodiment of FIG. 2*a*. The primary circuit 6 of the embodiment of FIG. 2*b* or 3 may also be used.

The secondary circuit 7' comprises six step-up levels, a first plurality of coupling capacitors 9*a*, 9*b*, 9*c*, 9*d*, 9*e*, 9*f* and a second plurality of (surge) capacitors 3*a*, 3*b*, 3*c*, 3*d*, 3*e*, 3*f*. Moreover, the secondary circuit 7' comprises a first plurality of diodes 4*a*, 4*b*, 4*c*, 4*d*, 4*e*, 4*f* and a second plurality of diodes 10*a*, 10*b*, 10*c*, 10*d*, 10*e*, 10*f*. However, unlike the embodiments of FIG. 2*b* and FIG. 3, the capacitors 9*a*, 9*b*, 9*c*, 9*d*, 9*e*, 9*f* are connected in parallel with each other instead of a series arrangement.

Thus, the voltages supplied by the capacitors can be better balanced compared to a series connection. The individual connections of the various semiconductor devices to each other can be seen in detail from the circuit diagram of FIG. 4.

Figure 1A:
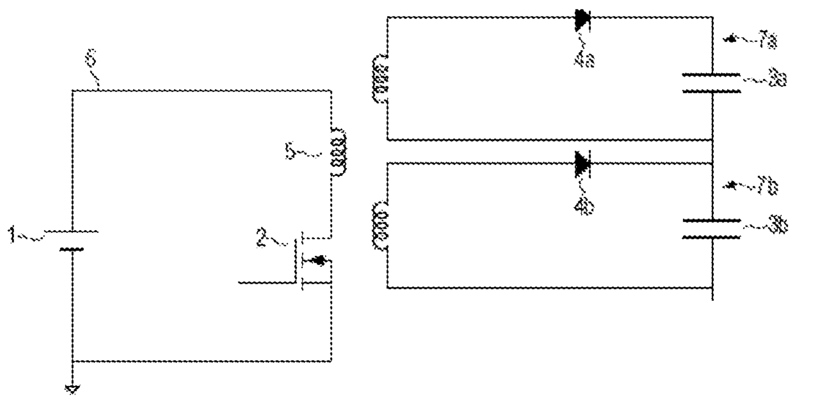
Figure 1B:
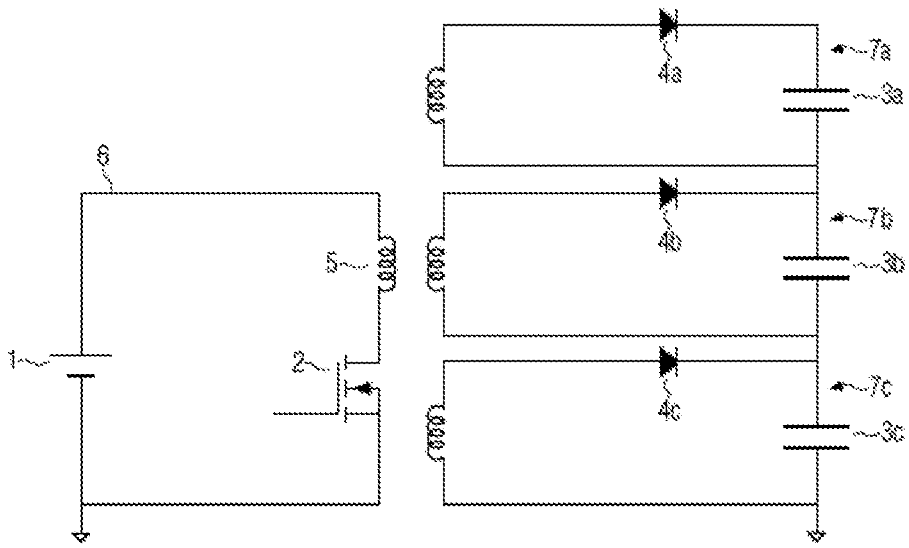

It should be noted that in the configurations shown in FIG. 2*a*, FIG. 2*b*, FIG. 3 and FIG. 4, a single secondary winding is required. The turn ratio n, of turns of the single secondary winding ns to the turns of the single primary winding np, is given by n=ns/np. It is preferably equal to two or more. The higher the turn ratio n, the more the voltage withstand constraints of the primary circuit 6 are relaxed. The switching device 2 must, for example, withstand 40 V to 60 V, which translates into a relatively moderate maximum channel resistance and low gate charge for a predefined control voltage of the transistor device comprised in the switching device. Battery voltages VA of approximately 3 V, 6 V or 9 V can be raised to output voltages VO of approximately 750 V or even 1500 V. The output energy provided by the discharge of the surge capacitors 3*a* through 3*f* (which may have capacitances in the range of, for example, 100 μF to 1 mF) may be in the range of, for example, 40 J to 100 J. The overall charging time can be less than 10 s. Electromagnetic interference due to current variations in the secondary circuit 7 can be kept to a level comparable to conventional "flyback" converters such as that described above with reference to FIG. 1*a* and FIG. 1*b*.

Figure 5:
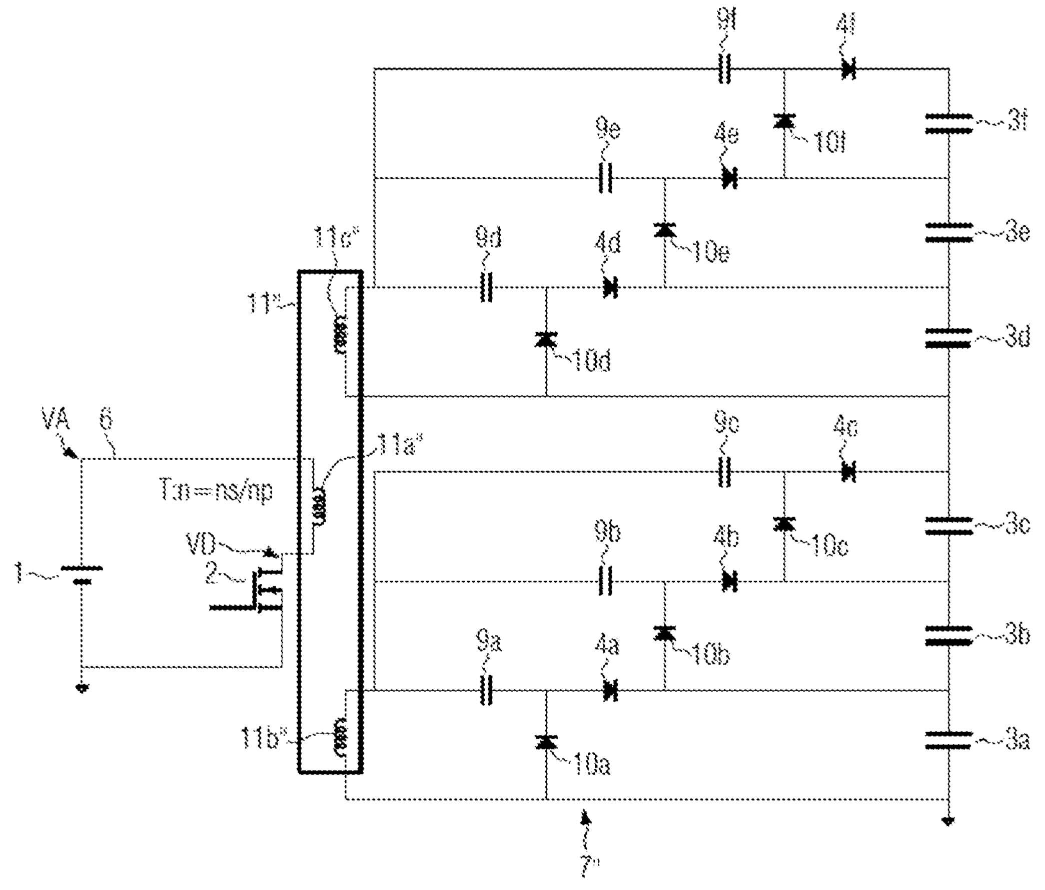
FIG. 5 represents a step-up converter with a plurality of levels of an implantable medical device comprising a transformer with two secondary windings and step-up levels according to a fourth embodiment of the present invention.

In the embodiments described hereinabove, a single secondary winding is comprised in the transformer of the step-up converter with a plurality of levels. However, the present invention is not limited to this. According to an alternative embodiment, more than one single secondary winding, for example, two secondary windings may be present. In this case, each winding of the secondary windings is associated with its plurality of step-up levels. FIG. 5 illustrates this configuration.

The step-up converter with a plurality of levels shown in FIG. 5 comprises a first circuit 6", at low voltage, and a second circuit 7", at high voltage, which are galvanically isolated from each other. The primary circuit 6" comprises a primary power source 1, in particular a DC source, for example, a battery or several batteries in series. The battery may be, for example, a lithium-manganese dioxide battery or a lithium-carbon monofluoride battery or a lithium-silver vanadium oxide battery and may provide a battery voltage VA in the range of 3 V, 6 V or 9 V. Moreover, the primary circuit 6" comprises a switching device 2, for example, comprising a transistor device, in particular, a MOSFET transistor. As shown in FIG. 2*b*, an additional inductance may be provided according to an alternative to reduce a current surge.

The step-up converter with a plurality of levels comprises a transformer 11". The transformer 11" comprises a primary winding 11*a*" with np turns or coil forming part of the primary circuit 6" and two secondary windings 11*b*" and 11*c*" or coils forming part of the secondary circuit 7".

Three step-up levels are associated with each of the secondary windings of the transformer 11". The three step-up levels shown at the bottom are associated with the secondary winding 11*b*" shown in FIG. 5 and comprise a first plurality of coupling capacitors 9*a*, 9*b*, 9*c*, a second plurality of surge capacitors 3*a*, 3*b*, 3*c*, a first plurality of diodes 4*a*, 4*b*, 4*c*, and a second plurality of diodes 10*a*, 10*b*, 10*c*. The other three step-up levels shown higher up are associated with the other of the secondary windings 11*c*" shown in FIG. 5 and comprise a first plurality of coupling capacitors 9*d*, 9*e*, 9*f*, a second plurality of surge capacitors 3*d*, 3*e*, 3*f*, a first plurality of diodes 4*d*, 4*e*, 4*f*, and a second plurality of diodes 10*d*, 10*e*, 10*f*.

In a manner similar to the embodiment shown in FIG. 4, the capacitors 9*a*, 9*b*, 9*c* and the capacitors 9*d*, 9*e*, 9*f* are, respectively, connected in parallel to each other. It should be noted that the example shown in FIG. 5 is symmetrical with respect to the number of step-up levels (three here) of the two pluralities of step-up levels associated with the two secondary windings. It is, however, conceivable that more or less step-up levels are associated with one of the secondary windings of the transformer 11 than with the other secondary winding.

According to one alternative, the capacitors 9*a* and/or 9*d* and the diodes 10*a* and/or 10*d* may be eliminated as in the embodiment of FIG. 2*a*.

The configuration shown in FIG. 5 is more complex than those shown in FIG. 2*a*, FIG. 2*b*, FIG. 3, and FIG. 4. The device can, however, operate in a more efficient manner. In particular, the maximum voltage of the coupling capacitor that needs to be charged to the highest level, see capacitor 9*f* in FIG. 4, can be reduced by 50%, respectively for capacitors 9*c* and 9*f* in the configuration shown in FIG. 5.

Figure 6:
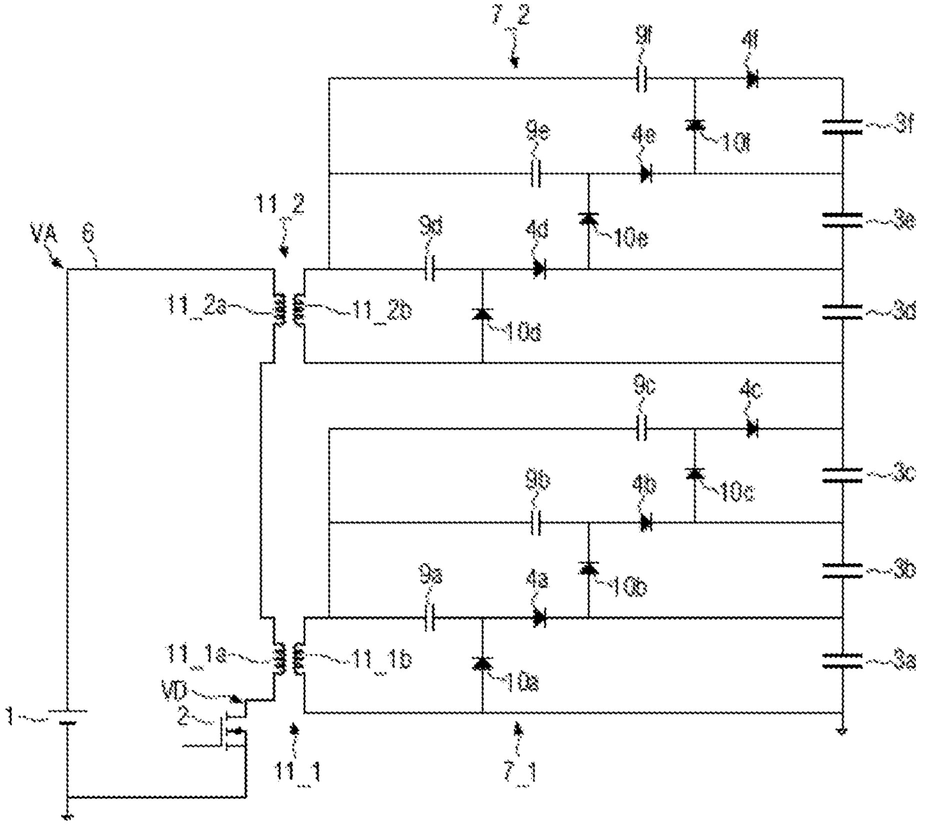
FIG. 6 represents a step-up converter with a plurality of levels of an implantable medical device comprising two transformers according to a fifth embodiment of the present invention.

Moreover, it should be noted that according to other embodiments, more than one transformer as shown in FIG. 2*a*, FIG. 2*b*, FIG. 3, FIG. 4 and FIG. 5 may be used in the step-up converter with a plurality of levels. In this case, the step-up converter with a plurality of levels may comprise a further transformer comprising another primary winding, in particular a further single primary winding, and another secondary winding, in particular a single secondary winding. FIG. 6 therefore depicts such a step-up converter with a plurality of levels of an implantable medical device comprising two transformers according to a fifth embodiment of the present invention.

In this fifth embodiment, the first circuit 6 comprises a primary power source 1 and a switching device 2 as in the first embodiments of the present invention. The converter likewise comprises two secondary circuits 7_1 and 7_2, each circuit having several step-up levels; here, by way of example, three step-up levels. In the embodiment of FIG. 6, the levels of the two secondary circuits are in parallel, as in the embodiment of FIG. 4 or FIG. 5. According to a variant, the levels of one of the two secondary circuits or of both secondary circuits may be in series as shown in FIG. 2*a*, FIG. 2*b* or FIG. 3.

The step-up converter with a plurality of levels comprises two transformers 11_1 and 11_2. Transformer 11_1 comprises a single primary winding 11_1*a* having np turns or coil being part of primary circuit 6 and a single secondary winding 11_1*b* with ns turns or coil forming part of the first secondary circuit 7_1. The transformer 11_2 comprises a single primary winding 11_2*a* with np turns or coil forming part of the primary circuit 6 and a single secondary winding 11_2*b* with ns turns or coil forming part of the second secondary circuit 7_2. In addition, the surge capacitors 3*c* and 3*d* are connected.

The embodiments of a step-up converter with a plurality of levels as described hereinabove can be used in an implantable defibrillator, in particular for a subcutaneous implantable cardioverter defibrillator, called S-ICD.

Figure 7:
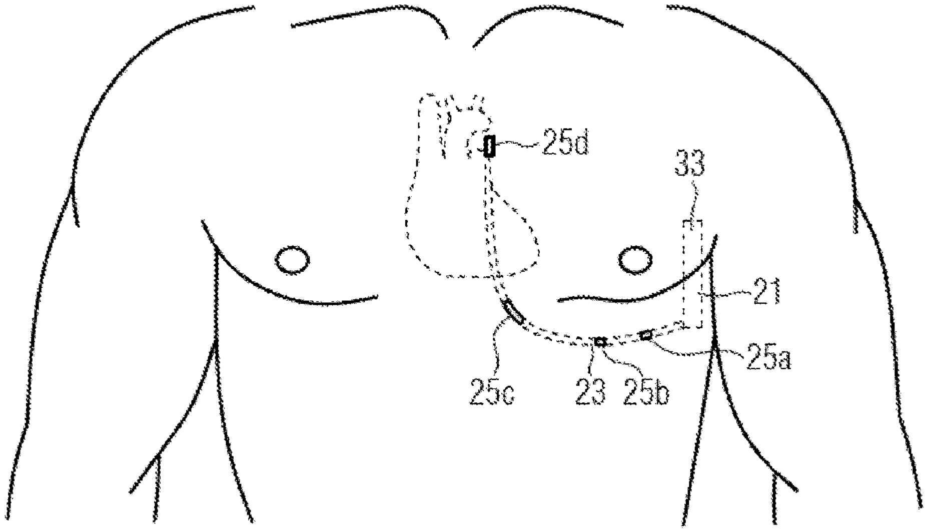
FIG. 7 represents an implantable defibrillator comprising a step-up converter with a plurality of levels according to one embodiment of the present invention.

An example of a subcutaneous implantable cardioverter defibrillator (S-ICD) 21 is illustrated in FIG. 7. The subcutaneous implantable cardioverter defibrillator (S-ICD) 21 comprises a step-up converter with a plurality of levels as described hereinabove, not visible in FIG. 7, a subcutaneous lead 23, and a metal housing 33. As shown in FIG. 7, the housing 33 is implanted subcutaneously. The subcutaneous lead 23 is arranged in the parasternal region. The subcutaneous lead 23 comprises a plurality of electrodes 25*a*, 25*b*, 25*c*, 25*d*. It should, however, be noted that the number of electrodes is not limiting. In one variant, the subcutaneous lead 23 may comprise fewer than four electrodes. In another variant, the subcutaneous probe 23 may comprise more than four electrodes.

At least one of the electrodes 25*a*, 25*b*, 25*c*, 25*d* may be a sensing electrode configured to sense electrophysiological signals. At least one of the electrodes 25*a*, 25*b*, 25*c*, 25*d* may be a defibrillation electrode capable of delivering a defibrillation signal.

In one variant, an electrical dipole may be formed between an electrode of the subcutaneous probe 23 and the housing 33.

In another variant (not shown), cardiac hemodynamic sensors, such as an accelerometer, may be integrated with the subcutaneous probe 23, as well as with the housing 33 in order to sense hemodynamic signals.

In the case of sensing of a fibrillation event, particularly by means of one or a plurality of the sensing electrodes 25*a*, 25*b*, 25*c*, 25*d*, and a suitably configured sensing circuit, not shown in FIG. 7, the subcutaneous implantable cardioverter defibrillator (S-ICD) 21 is activated. Shocks may be delivered to the heart by means of a defibrillation electrode of the subcutaneous lead 23 by a shock circuit that is connected to the charged capacitors of one of the embodiments of the step-up converter with a plurality of levels described hereinabove. The shocks are delivered under the control of the control unit, not shown in FIG. 7, comprised in the subcutaneous implantable cardioverter defibrillator (S-ICD) 21. The control unit also controls the charging operation of the step-up converter with a plurality of levels of the subcutaneous implantable cardioverter defibrillator (S-ICD) 21.

All of the embodiments discussed hereinabove are not intended to be limitations but serve as illustrative examples of features and advantages of the invention. It should be understood that some or all of the features described hereinabove may also be combined in different ways.

The invention claimed is:

1. A step-up converter with a plurality of levels disposed in an implantable defibrillator, the step-up converter comprising:

a transformer comprising a single primary winding and a single secondary winding;

a primary circuit comprising the single primary winding, a primary power source connected in series with the single primary winding, and a switching device connected in series with the single primary winding; and a secondary circuit comprising the single secondary winding and a plurality of step-up levels;

wherein each step-up level comprises a first diode, a second diode, a first capacitor, and a second capacitor interconnected such that:

an anode of the first diode is connected to a terminal of the first capacitor and to a cathode of the second diode;

the second capacitor is connected between a cathode of the first diode and an anode of the second diode; and the second capacitors of the plurality of step-up levels are connected in series;

wherein the primary circuit additionally comprises an inductor connected in series with the single primary winding and the switching device;

wherein closing the switching device establishes a current path including the primary power source, the inductor, the single primary winding, and the switching device, and opening the switching device interrupts the current path;

wherein the first capacitors are coupling capacitors and the second capacitors are surge capacitors configured to store energy for delivery of a shock by the implantable defibrillator; and wherein the inductor is configured to reduce a current surge when the switching device is closed at a beginning of a first period during which the first capacitors are charged, via the second diodes, to voltages of respective second capacitors. and wherein, during a second period immediately following the first period and during which the switching device is open, energy is transferred from the first capacitors and the single secondary winding to the second capacitors.

2. The step-up converter of claim 1, further comprising an additional step-up level that consists of only one capacitor and only one diode, the capacitor having a first terminal directly connected to a first terminal of the single secondary winding and the diode linking a second terminal of the capacitor to a second terminal of the single secondary winding.

3. The step-up converter of claim 1, wherein the step-up converter with a plurality of levels is configured to step up a voltage of the primary power source in the range of 1 V to 9 V to an output voltage provided by the second capacitors of the step-up levels in the range of 10 V to 100 V or in the range 100 V to 2000 V.

4. The step-up converter of claim 1, wherein a turn ratio of a single primary winding np to a single secondary winding ns, is ns/np≥2.

5. The step-up converter of claim 1, wherein the primary circuit and the secondary circuit are galvanically isolated from each other.

6. The step-up converter of claim 1, wherein the switching device comprises a transistor device.

7. The step-up converter of claim 1, wherein the primary circuit comprises a first sensing means for sensing a current flowing in the first winding and a second means for sensing oscillations at the terminals of the switching device.

8. The step-up converter of claim 1 further comprising another transformer comprising another primary winding and another secondary winding.

9. The step-up converter of claim 1, wherein the first capacitors of the step-up levels of the secondary circuit are connected in parallel with each other.

10. A step-up converter with a plurality of levels disposed in a subcutaneous implantable defibrillator, the step-up converter comprising:

a transformer comprising a single primary winding and at least two secondary windings;

a primary circuit comprising the single primary winding and a switching device, and a secondary circuit comprising the secondary windings and a plurality of step-up levels, the plurality of step-up levels comprising a first plurality of step-up levels associated with a first one of the at least two secondary windings and a second plurality of step-up levels associated with a second one of the at least two secondary windings, each step-up level comprising a first diode, a second diode, a first capacitor, and a second capacitor interconnected such that:

an anode of the first diode is connected to a terminal of the first capacitor and to a cathode of the second diode;

a terminal of the second capacitor is connected to a cathode of the first diode; and another terminal of the second capacitor is connected to an anode of the second diode; and wherein second capacitors of the plurality of step-up levels are connected in series and are surge capacitors configured to store energy for delivery of a shock by the subcutaneous implantable defibrillator;

wherein first capacitors of the first plurality of step-up levels are connected in parallel with one another, and first capacitors of the second plurality of step-up levels are connected in parallel with one another.

11. The step-up converter of claim 10, further comprising an additional step-up level that consists of only one capacitor and only one diode, the capacitor being directly connected to one terminal of the one of the secondary windings, and the diode linking the other terminal of the capacitor to the other terminal of the same secondary winding.

12. A method for operating a step-up converter with a plurality of levels disposed in an implantable defibrillator the step-up converter comprising:

a transformer having a single primary winding and a single secondary winding;

a primary circuit including the single primary winding, a primary power source connected in series with the single primary winding, and a switching device connected in series with the single primary winding, and an inductor connected in series with the single primary winding and the switching device; and a secondary circuit comprising the single secondary winding and a plurality of step-up levels, each step-up level comprising a first diode, a second diode, a first capacitor, and a second capacitor interconnected such that (i) an anode of the first diode is connected to a terminal of the first capacitor and to a cathode of the second diode, (ii) a terminal of the second capacitor is connected to a cathode of the first diode, and (iii) another terminal of the second capacitor is connected to an anode of the second diode; and wherein second capacitors of the plurality of step-up levels are connected in series and are surge capacitors configured to store energy for delivery of a shock by the implantable defibrillator, the method comprising the steps of:

a) closing the switching device during a first period such that the single primary winding stores energy according to a peak value of current in the primary circuit and the first capacitors are charged via the second diodes to voltages of the respective second capacitors;

b) opening the switching device during a second period immediately after the first period such that energy is transferred from the first capacitors and the single secondary winding to the second capacitors; and (c) repeating steps a) and b) until a predefined output voltage is provided by the series-connected second capacitors; wherein closing the switching device establishes a current path including the primary power source, the inductor, the single primary winding, and the switching device, and opening the switching device interrupts the current path;

wherein, during the repeating, the inductor reduces a current surge occurring when the switching device is closed; and wherein, over all or part of the repeating, at least one of (i) a duration of the first period or (ii) the peak value of current in the primary circuit progressively increases.

13. The method of claim 12, wherein the duration of the first period is initially shorter than the second period and progressively increases during charging of the surge capacitors.

14. The method of claim 12, wherein the maximum of the current (Ip) in the primary circuit is initially set to a first value at a beginning of a charging cycle of the surge capacitors and progressively increases to a second value greater than the first value before completion of the charging cycle.

* * * * *